US011400294B2

(12) United States Patent
McDonald et al.

(10) Patent No.: US 11,400,294 B2
(45) Date of Patent: Aug. 2, 2022

(54) METHOD AND APPARATUS FOR NEUROSTIMULATION DEVICE THERAPY MANAGEMENT

(71) Applicant: Boston Scientific Neuromodulation Corporation, Valencia, CA (US)

(72) Inventors: Matthew Lee McDonald, Pasadena, CA (US); Bradley Lawrence Hershey, Carrollton, TX (US); Dennis Zottola, Ventura, CA (US); Dat Thanh Huynh, West Hollywood, CA (US); Natalie Bloom Lyons, Sauk Rapids, MN (US); Juan Gabriel Hincapie Ordonez, Maple Grove, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 282 days.

(21) Appl. No.: 16/392,891

(22) Filed: Apr. 24, 2019

(65) Prior Publication Data

US 2019/0344080 A1 Nov. 14, 2019

Related U.S. Application Data

(60) Provisional application No. 62/669,041, filed on May 9, 2018.

(51) Int. Cl.
*A61N 1/36* (2006.01)
*A61B 5/11* (2006.01)
(Continued)

(52) U.S. Cl.
CPC ........ *A61N 1/36139* (2013.01); *A61B 5/1118* (2013.01); *A61B 5/369* (2021.01);
(Continued)

(58) Field of Classification Search
CPC ............ A61N 1/36139; A61N 1/36071; A61N 1/36175; A61N 1/0534; A61N 1/36132;
(Continued)

(56) References Cited

U.S. PATENT DOCUMENTS

| 7,155,277 B1 * | 12/2006 | Brewer | G16H 10/60 |
| | | | 607/2 |
| 2008/0004904 A1 * | 1/2008 | Tran | A61B 8/565 |
| | | | 705/2 |

(Continued)

FOREIGN PATENT DOCUMENTS

| WO | WO-2018132529 A1 | 7/2018 |
| WO | WO-2019217071 A1 | 11/2019 |

OTHER PUBLICATIONS

"International Application Serial No. PCT/US2019/028838, International Preliminary Report on Patentability dated Nov. 19, 2020", 8 pgs.

(Continued)

*Primary Examiner* — Amanda K Hulbert
*Assistant Examiner* — Natasha Patel
(74) *Attorney, Agent, or Firm* — Schwegman Lundberg & Woessner, P.A.

(57) ABSTRACT

An example of a neurostimulation system may include one or more sensing devices and a patient assistance device. The sensing device(s) may be configured to sense one or more signals from a patient and may include one or more non-invasive sensing devices. The patient assistance device may be configured to assist the patient in use of a stimulation device and may include a communication circuit configured to receive the sensed signal(s), a user interface configured to allow for interactions with the patient, and a processing circuit which may be configured to receive patient-specific information including the sensed signal(s), to analyze the patient-specific information with neurostimulation algo-
(Continued)

rithm information representative of available therapeutic options, to produce one or more recommendations related to use of the stimulation device for treating the patient based on the analysis, and to present at least one recommendation using the user interface.

20 Claims, 11 Drawing Sheets

(51) Int. Cl.
  *A61B 5/00* (2006.01)
  *A61B 5/369* (2021.01)
  *G16H 20/30* (2018.01)
  *A61N 1/05* (2006.01)
(52) U.S. Cl.
  CPC ........ *A61B 5/4836* (2013.01); *A61N 1/36071* (2013.01); *A61N 1/36175* (2013.01); *A61B 5/4812* (2013.01); *A61N 1/0534* (2013.01); *A61N 1/36132* (2013.01); *G16H 20/30* (2018.01)
(58) Field of Classification Search
  CPC ............ A61N 1/37282; A61N 1/36128; A61N 1/0551; A61N 1/36062; A61N 1/36185; A61N 1/37247; A61B 5/369; A61B 5/1118; A61B 5/4836; A61B 5/4812; A61B 5/24; A61B 5/6898; A61B 5/7475; A61B 2505/09; A61B 2562/164; A61B 5/002; A61B 5/0022; A61B 5/4848; A61B 5/486; A61B 5/681; A61B 5/686; G16H 20/30; G16H 40/67
  See application file for complete search history.

(56) References Cited

U.S. PATENT DOCUMENTS

| | | | |
|---|---|---|---|
| 2014/0213926 A1* | 7/2014 | Vaidyanathan | .... A61N 1/36135 600/545 |
| 2014/0214111 A1* | 7/2014 | Greiner | .............. A61N 1/36175 607/30 |
| 2014/0358194 A1* | 12/2014 | Vansickle | .......... A61N 1/36034 607/59 |
| 2016/0045746 A1 | 2/2016 | Jiang et al. | |
| 2016/0213314 A1* | 7/2016 | Zuckerman-Stark | ........................ A61N 1/36139 |
| 2017/0021172 A1* | 1/2017 | Perez | ................. A61N 1/36031 |
| 2017/0239486 A1 | 8/2017 | Suryavanshi | |
| 2018/0043172 A1 | 2/2018 | Serrano Carmona | |
| 2018/0085584 A1 | 3/2018 | Thakur et al. | |
| 2018/0193651 A1 | 7/2018 | Annoni et al. | |
| 2018/0229040 A1 | 8/2018 | Srivastava et al. | |

OTHER PUBLICATIONS

"International Application Serial No. PCT/US2019/028838, International Search Report dated Aug. 16, 2019", 4 pgs.

"International Application Serial No. PCT/US2019/028838, Written Opinion dated Aug. 16, 2019", 6 pgs.

"Australian Application Serial No. 2019266088, First Examination Report dated May 31, 2021", 5 pgs.

"European Application Serial No. 19728773.3, Response filed Jun. 18, 2021 to Communication pursuant to Rules 161(1) and 162 EPC dated Dec. 22, 2021", 12 pgs.

"Australian Application Serial No. 2019266088, Response filed Nov. 30, 2021 to First Examination Report dated May 31, 2021", 17 pgs.

* cited by examiner

METHOD AND APPARATUS FOR NEUROSTIMULATION DEVICE THERAPY MANAGEMENT

CLAIM OF PRIORITY

This application claims the benefit of priority under 35 U.S.C. § 119(e) of U.S. Provisional Patent Application Ser. No. 62/669,041, filed on May 9, 2018, which is herein incorporated by reference in its entirety.

TECHNICAL FIELD

This document relates generally to medical devices and more particularly to a system for identifying a patient for a therapy delivered by a medical device and adjusting the medical device for therapy delivery customized for the patient.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostitnulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. The human nervous systems use neural signals having sophisticated patterns to communicate various types of information, including sensations of pain, pressure, temperature, etc. It may interpret an artificial stimulation with a simple pattern of stimuli as an unnatural phenomenon, and respond with an unintended and undesirable sensation and/or movement. Also, as the condition of the patient may change while receiving a neurostimulation therapy, the pattern of neurostimulation pukes applied to the patient may need to be changed to maintain efficacy of the therapy while minimizing the unintended and undesirable sensation and/or movement. While modern electronics provides technology needed for producing a stimulation device that can generate sophisticated pulse patterns emulating natural patterns of neural signals observed in the human body, utilization of capability of such a device depends on the expertise of its users to a great extent. For example, a sophisticated pulse pattern may only benefit a patient when it is customized for that patient and updated timely in response to changes in the patient's conditions and needs. This makes programming and re-programming of the stimulation device for the patient a challenging task.

SUMMARY

An example (e.g., "Example 1") of a system for managing use of a stimulation device configured for delivering neurostimulation to a patient may include one or more sensing devices and a patient assistance device. The one or more sensing devices may be configured to sense one or more signals from the patient and may include one or more non-invasive sensing devices. The patient assistance device may be configured to assist the patient in use of the stimulation device and may include a communication circuit, a user interface, and a processing circuit. The communication circuit may be configured to receive the sensed one or more signals from the one or more sensing devices. The user interface may be configured to allow for interactions between the patient assistance device and the patient. The processing circuit may be configured to receive patient-specific information including the sensed one or more signals, to analyze the received patient-specific information with neurostimulation algorithm information representative of available therapeutic options using the stimulation device, to produce one or more recommendations related to use of the stimulation device for treating the patient based on one or more outcomes of the analysis, and to present at least one recommendation of the produced one or more recommendations using the user interface.

In Example 2, the subject matter of Example 1 may optionally be configured such that the patient assistance device includes a mobile device.

In Example 3, the subject matter of Example 2 may optionally be configured such that the patient assistance device is implemented in a smartphone.

In Example 4, the subject matter of any one or any combination of Examples 1 to 3 may optionally be configured such that the stimulation device includes an implantable stimulation device, and the communication circuit of the patient assistance device is configured to allow for direct communications between the patient assistance device and the stimulation device.

In Example 5, the subject matter of any one or any combination of Examples 1 to 3 may optionally be configured such that the stimulation device includes an implantable stimulation device, the system further includes a remote control configured to be used by the patient to adjust the implantable stimulation device, and the communication circuit of the patient assistance device is configured to allow for direct communications between the patient assistance device and the remote control.

In Example 6, the subject matter of any one or any combination of Examples 4 and 5 may optionally be configured such that the one or more sensing devices further includes one or more implantable sensing devices.

In Example 7, the subject matter of any one or any combination of Examples 1 to 6 may optionally be configured such that the one or more non-invasive sensing devices include a skin patch configured to be attached to the patient.

In Example 8, the subject matter of any one or any combination of Examples 1 to 7 may optionally be configured such that the one or more non-invasive sensing devices include a wrist-worn device.

In Example 9, the subject matter of any one or any combination of Examples 1 to 8 may optionally be configured to further include a plurality of databases and a telecommunication system configured to communicatively couple the patient assistance device to the plurality of databases. The plurality of databases includes a patient database containing portions of the patient-specific information and a neurostinulation algorithm database containing portions of the neurostimulation algorithm information.

In Example 10, the subject matter of Example 9 may optionally be configured to further include a plurality of web portals each configured to allow a type of users of a plurality of types of users to participate in the treatment of the patient using the stimulation device.

In Example 11, the subject matter of Example 10 may optionally be configured such that the processing circuit of the patient assistance device is further configured to produce at least one recommendation for initial settings of the stimulation device including at least a type of the stimulation device, a stimulation program, and parameters used by the stimulation program.

In Example 12, the subject matter of Example 11 may optionally be configured such that the processing circuit of the patient assistance device is further configured to optimize the settings of the stimulation device for the patient after the neurostimulation is delivered to the patient.

In Example 13, the subject matter of Example 12 may optionally be configured such that the processing circuit of the patient assistance device is further configured to maintain optimization of the settings of the stimulation device for the patient throughout the use of the stimulation device for the patient.

In Example 14, the subject matter of any one or any combination of Examples 11 to 13 may optionally be configured such that the processing circuit of the patient assistance device is further configured to detect a problem based on the patient-specific information received after the neurostimulation is delivered to the patient and to identify a user of the plurality of users who is suitable for addressing the detected problem based on a type of the detected problem, and to communicate to the identified user about the detected problem through the telecommunication system and a web portal of the plurality of web portals.

In Example 15, the subject matter of any one or any combination of Examples 11 to 14 may optionally be configured such that the processing circuit of the patient assistance device is further configured to identify complementary activities and behaviors to be combined with the neurostimulation delivered from the stimulation device to enhance outcome of the neurostimulation, and to recommend the identified activities and behaviors to the patient using the user interface of the patient assistance device.

An example (e.g., "Example 16") of a method for managing use of a stimulation device configured for delivering neurostimulation to a patient is also provided. The method may include sensing one or more signals from the patient using one or more non-invasive sensing devices worn by the patient, transmitting the sensed one or more signals to a patient assistance device provided to the patient, analyzing patient-specific information with neurostimulation algorithm information using the patient assistance device, producing one or more recommendations related to use of the stimulation device for treating the patient based on one or more outcomes of the analysis, and presenting at least one recommendation of the produced one or more recommendations to the patient, the at least one recommendation indicating whether the use of the stimulation device is recommended for treating the patient. The patient-specific information may include the sensed one or more signals. The neurostimulation algorithm information may be representative of available therapeutic options using the stimulation device.

In Example 17, the subject matter of Example 16 may optionally further include receiving the patient-specific information, including presenting one or more questions to the patient and receiving one or more answers from the patient using the patient assistance device.

In Example 18, the subject matter of receiving the patient-specific information as found in Example 17 may optionally further include receiving information from a patient database accessible using the patient assistance device.

In Example 19, the subject matter of any one or any combination of Examples 16 to 18 may optionally further include receiving the neurostimulation algorithm information from a neurostimulation algorithm database accessible using the patient assistance device.

In Example 20, the subject matter of producing the one or more recommendations as found in any one or any combination of Examples 16 to 18 may optionally further include producing a recommendation for initial settings of the stimulation device.

In Example 21, the subject matter of Example 20 may optionally further include programming the stimulation device based on the recommended initial settings and delivering neurostimulation from the programmed stimulation device.

In Example 22, the subject matter of Example 21 may optionally further include producing a recommendation for customizing the settings of the stimulation device using the one or more signals sensed after a beginning of the delivery of the neurostimulation.

In Example 23, the subject matter of Example 22 may optionally further include teaching the patient on how to adjust the settings of the stimulation device using a touchscreen of the patient assistance device.

In Example 24, the subject matter of any one or any combination of Examples 16 to 23 may optionally further include communicatively coupling the patient assistance device to a network including portals accessible by users each specialized in one or more fields related to the use of the stimulation device, identifying a problem associated with the use of the stimulation device, identifying a user from the users who is considered suitable for addressing the identified problem, and notifying the identified user by one or more of communicating to the user through the network directly or presenting instructions on contacting the identified user using the patient assistance device.

In Example 25, the subject matter of any one or any combination of Examples 16 to 24 may optionally further include implementing the patient assistance device as a mobile device.

An example (e.g., "Example 26") of a non-transitory machine readable medium including instructions, which when operated on by a machine, cause the machine to perform a method, is also provided. The method may include sensing one or more signals from a patient using one or more non-invasive sensing devices worn by the patient, transmitting the sensed one or more signals to a patient assistance device provided to the patient, analyzing patient-specific information with neurostimulation algorithm information using the patient assistance device, producing one or more recommendations related to use of a stimulation device for treating the patient based on one or more outcomes of the analysis, and presenting at least one recommendation of the produced one or more recommendations to the patient, the at least one recommendation indicating whether the use of the stimulation device is recommended for treating the patient. The patient-specific information may include the sensed one or more signals. The neurostimulation algorithm information may be representative of available therapeutic options using the stimulation device.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
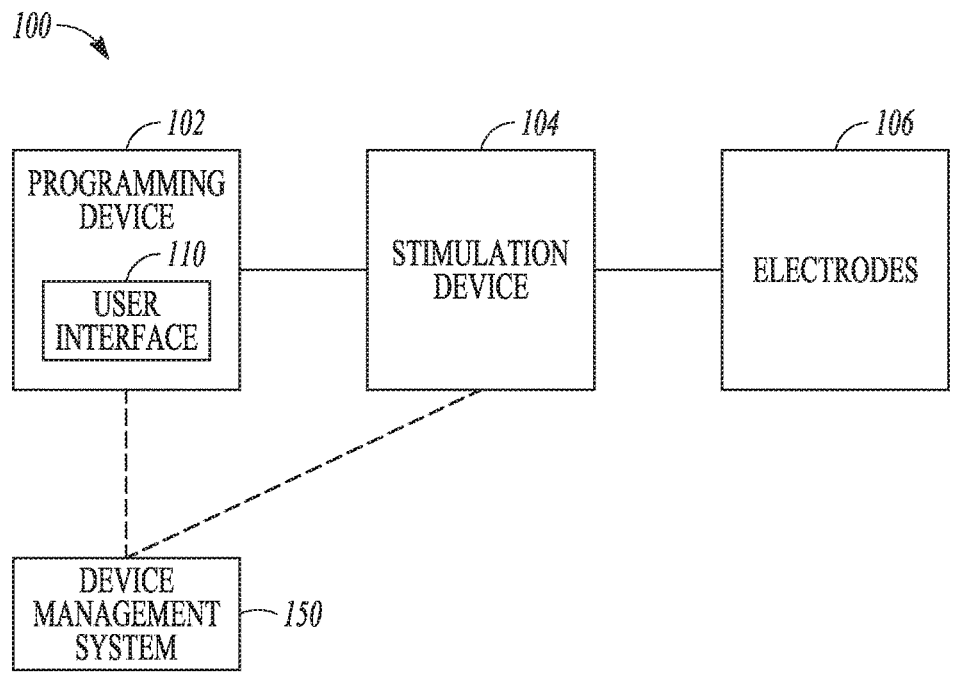
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a system that includes medical devices delivering therapies to patients and links the medical devices and the patients to users such as clinicians, device manufacturer's representatives, research and development scientists and engineers, and supporting staff for optimizing therapy delivery for each patient to meeting the patient's changes conditions and needs. While spinal cord stimulation (SCS) is used as a specific example for the purpose of illustration and discussion, the present system can be used for any neuromodulation and other therapies whose efficacy can be improved by applying the adjustment or optimization techniques discussed in this document. Examples of such neuromodulation therapies besides SCS can include deep brain stimulation (DBS), peripheral nerve stimulation (PNS), peripheral nerve field stimulation, functional electrical stimulation (FES), vagus nerve stimulation (VNS), autonomic nerve stimulation (ANS), hypoglossal nerve stimulation (HNS), and sacral nerve stimulation (SNS).

Today, the capability of a neuromodulation system for delivering SCS is often underutilized. In various examples, an existing SCS system knows too little about the patient to help increase utilization of its capability. As a result, SCS is often considered as a last resource in treating various disorders even though these disordered are indicated for SCS. For example, SCS has been proven to be an effective therapy for treating some forms of chronic pain. Examples of other therapies treating chronic pain include medication, surgery or other interventional procedures such as nerve block injections, radio frequency ablation, exercise, nutritional adjustments, mindfulness training (e.g., yoga), physical therapy and rehabilitation, acupuncture, biofeedback therapy, and massage therapy. Such therapies may be preferred because they are easier to apply, rather than being more effective than SCS. Therefore, there is a need for facilitating customization and optimization of SCS for each patient such that the potential benefit of SCS can be maximized for the patient.

Many challenges exist in meeting such a need. Examples of such challenges can include identifying patients that may respond to SCS, selecting stimulation programs to try for each identified patient, tailoring a selected program to each patient to meet the patient's ongoing needs with minimal burden on the patient's attending caregiver, updating the patient's therapeutic system with best programming practices as they become available, ensuring the best programming practices are used for the patient, guiding the patient to correctly use and adjust his/her system, and keeping the patient's healthcare provider up to date with and involved in the operation of the system while the patient is at home or otherwise remote from the healthcare provider's facilities.

The present system addresses such challenges by providing a "digital ecosystem" that links each patient to various types of users such that the patient's changing conditions, needs, and issues can be communicated to relevant users while knowledge of various aspects of the system is available for optimizing SCS and/or one or more other therapies for the patient. The present system can have the potential of creating a comprehensive therapy plan treating the patient based on his/her disease state, rather than treating only the neuropathic component.

In one embodiment, the present system provides each patient with guidance in using his/her SCS system. For example, an implantable neurostimulator can be placed in a patent. The implantable stimulator can include one or more sensors, or one or more separate implantable sensors can also be placed in the patient. One or more external sensors such as one or more wearable sensors can also be provided to the patient. The patient is provided with an integrated coach mobile based application (web, smartphone or smartwatch) that can read information from the implanted neurostimulator, the one or more implantable sensors, and/or the one or more wearable sensors and provide coaching instructions on how to optimize treatment modalities by suggesting changes to their neurostimulation paradigms as well as other applicable strategies (e.g., adjusting daily activities and incorporating other therapies) for a successful overall therapeutic outcome.

FIG. 1 illustrates an embodiment of a neurostimulation system 100. System 100 includes electrodes 106, a stimulation device 104, a programming device 102, and a device management system 150. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of electrical pulses and a selection of electrodes through which each of the electrical pulses is delivered. In various embodiments, at least some parameters of the plurality of stimulation parameters are programmable by a user, such as a clinician who treats the patient using system. Programming device 102 provides the user with accessibility to the user-programmable parameters. In various embodiments, programming device 102 is configured to be communicatively coupled to stimulation device via a wired or wireless link. Device management system 150 can provide users and the patient with support in setting stimulation device 104 using various resources to maximize benefits of neurostimulation for the patient.

In this document, a "user" can include any person involved in research, development, and application of system 100, and a "patient" can include any person who receives or is evaluated for receiving one or more therapies using system 100. For the purpose of discussion below. "the user" may refer to any one or more persons each being such a user, and may refer to the same person or a different person. Examples of the users can include physicians, nurses, other clinical personnel, clinical representatives of device provider, neurostimulation researchers, biomedical engineers and other device specialists, and any other persons capable of contributing to the care of the patient using system 100. In various embodiments, some users are authorized to determine settings of stimulation device 104 for application and adjustment of therapy using system 100, while other users can support the application and adjustment of therapy in various ways such as improving device capabilities, recommending new therapies and/or therapy parameters, and addressing problems that occur during the therapy.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

Device management system 150 can communicate with programming device 102 and/or stimulation device 104 directly and/or through a user or the patient. In various embodiments, device management system 150 can provide users and/or the patient in determining whether a therapy using stimulation device 104 is suitable for the patient, determining initial settings of stimulation device 104 including initial values for the plurality of stimulation parameters, customizing the settings of stimulation device 104, and/or monitoring conditions of the patient and operation of stimulation device 104 during the therapy and making timely adjustments. In various embodiments, device management system 150 allows various types of users to participate in managing the therapy delivered from stimulation device 104 to the patient from different physical locations. In various embodiments, device management system 150 can include a device provided to the patient to assist the patient in making various therapy-related decisions and optimizing patient-controllable settings of stimulation device 104.

In various embodiments, system 100 can be configured for neurostimulation applications, including but not limited to SCS, DBS, PNS, and FES applications. User interface 110 can be configured to allow the user to control the operation of system 100 for neurostimulation. Device management system 150 can be used to program stimulation device 104 directly and/or through the user and/or the patient using user interface 110.

Figure 2:
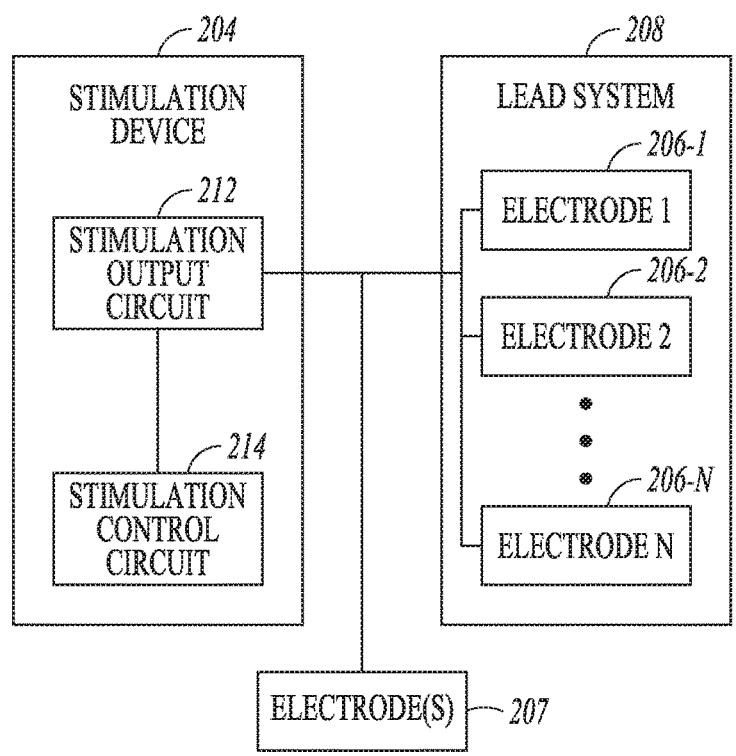
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 can represent an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 16 electrodes.

Figure 3:
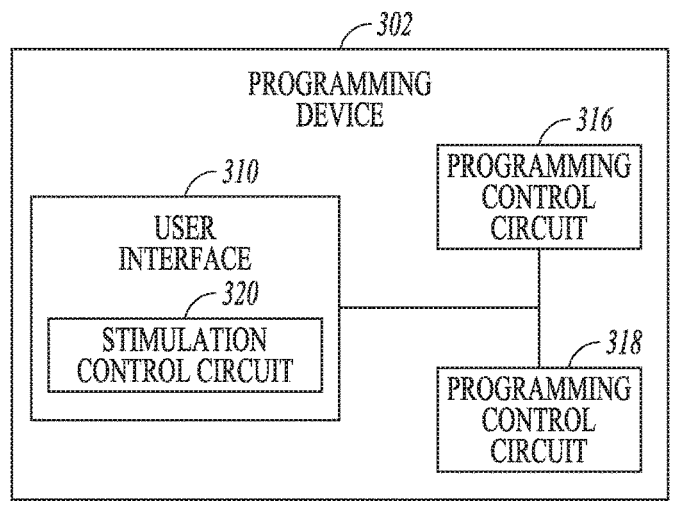
FIG. 3 illustrates an embodiment of a programming device, such as may be implemented in the neurostitnulation system of FIG. 1.

FIG. 3 illustrates an embodiment of a programming device 302, such as may be implemented in neurostimulation system 100. Programming device 302 can represent an example of programming device 102 and includes a storage device 318, a programming control circuit 316, and a user interface 310. Programming control circuit 316 generates the plurality of stimulation parameters that controls the delivery of the neurostimulation pulses according to a specified stimulation program that can define, for example, stimulation waveform and electrode configuration. User interface 310 can represent an example of user interface 110 and includes a stimulation control circuit 320. Storage device 318 stores instructions for operating programming device 302 and information used by programming control circuit 316 and stimulation control circuit 320, such as one or more stimulation programs and information about a stimulation device that relates the stimulation program to the plurality of stimulation parameters and information relating each of the stimulation programs to target tissue in the patient. In various embodiments, stimulation control circuit 320 can be configured to support one or more functions allowing for programming of stimulation devices, such as stimulation device 104 including but not limited to its various embodiments as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "stimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

Figure 4:
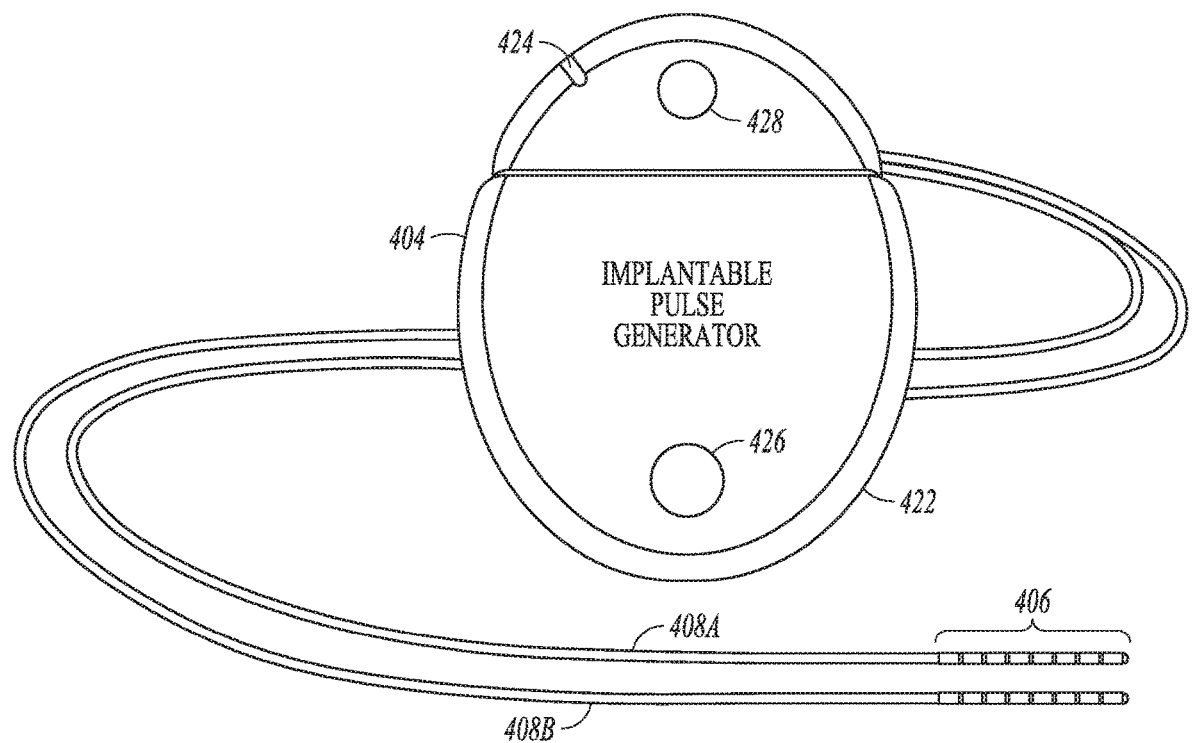
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 4, leads 408A and 408B each include 16 electrodes 406 at the distal end. The number and arrangement of leads 408A and 408B and electrodes 406 as shown in FIG. 4 are only an example, and other numbers and arrangements are possible. In various embodiments, the electrodes are ring electrodes. The implantable leads and electrodes may be configured by shape and size to provide electrical neurostimulation energy to a neuronal target included in the subject's brain, or configured to provide electrical neurostimulation energy to a nerve cell target included in the subject's spinal cord.

IPG 404 can include a hermetically-sealed IPG case 422 to house the electronic circuitry of IPG 404, an electrode 426 formed on IPG case 422, and an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of either lead 408A or lead 408B. Neurostimulation energy can be delivered in multipolar mode using one or more electrodes of a lead (e.g., one or more electrodes of lead 408A) as cathodes and one or more electrodes of the same or a different lead (e.g., one or more electrodes of lead 408B) as anodes.

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), which includes intra-burst or interburst rate parameters, amplitudes of pulses in the pulse train, polarity of the pulses, ramp on/off times, time/duty cycles, etc.

Figure 5:
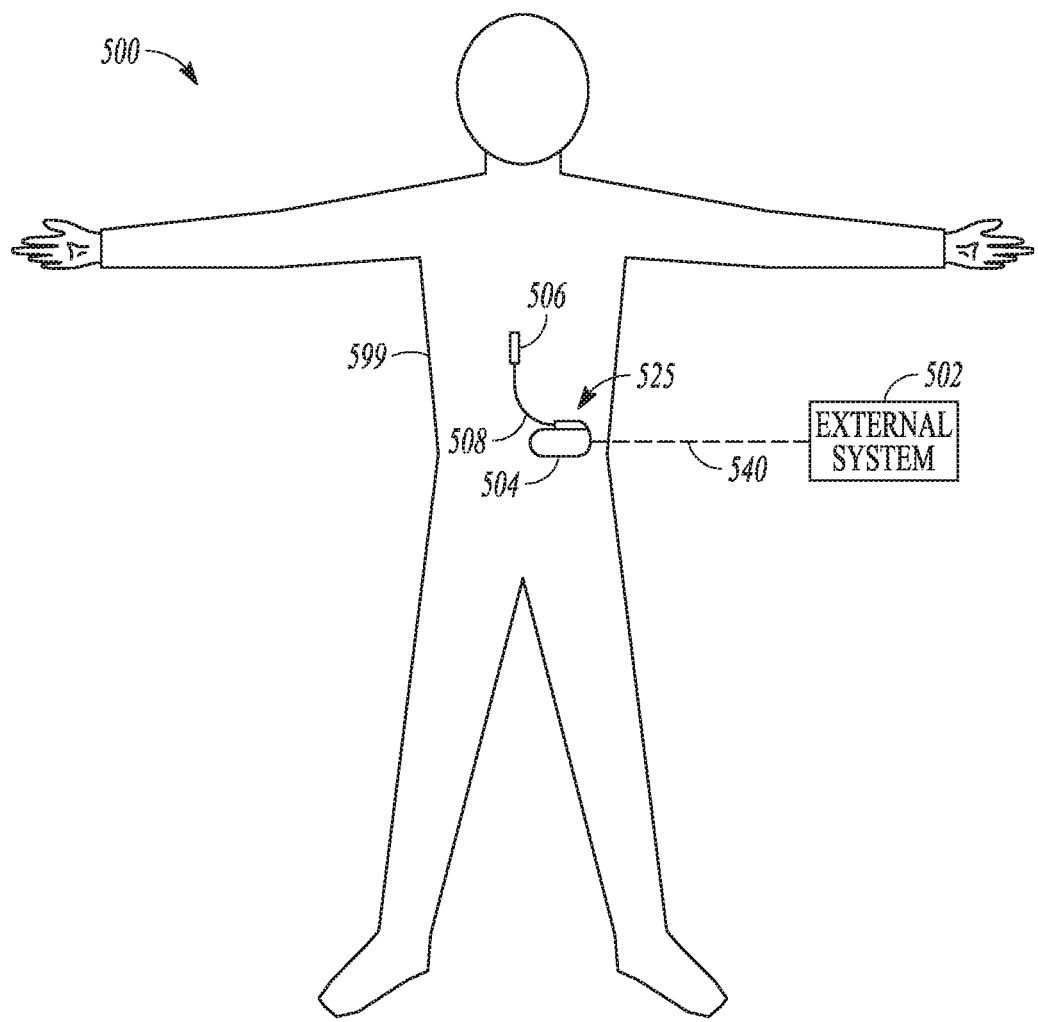
FIG. 5 illustrates an implantable neurostimulation system, such as an example application of the IPG and implantable lead system of FIG. 4, and portions of an environment in which the system may be used.

FIG. 5 illustrates an implantable neurostimulation system 500 and portions of an environment in which system 500 may be used. System 500 includes an implantable system 525, an external system 502, and a telemetry link 540 providing for wireless communication between implantable system 525 and external system 502. Implantable system 525 is illustrated in FIG. 5 as being implanted in the patient's body 599.

An example of IPG 504 includes IPG 404. An example of lead system 508 includes one or more of leads 408A and 408B. In the illustrated embodiment, implantable lead system 508 is arranged to provide SCS to a patient, with the stimulation target being neuronal tissue in the patient's spinal cord. In various embodiments, the present subject matter can be applied to neurostimulation of any types and targets, including but not limited to SCS, DBS, ITS, and FES.

Implantable system 525 includes an implantable stimulator (also referred to as an IPG) 504, a lead system 508, and electrodes 506, which can represent an example of stimulation device 204, lead system 208, and electrodes 206, respectively. External system 502 can represent an example of programming device 302. In various embodiments, external system 502 can include one or more external (non-implantable) devices each allowing the user and/or the patient to communicate with implantable system 525. In some embodiments, external system 502 includes a programming device intended for the user to initialize and adjust settings for implantable stimulator 504 and a remote control device intended for use by the patient. For example, the remote control device may allow the patient to turn implantable stimulator 404 on and off and/or adjust certain patient-programmable parameters of the plurality of stimulation parameters.

The sizes and shapes of the elements of implantable system 525 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regardless of stimulation targets in the patient's body and whether the stimulation device is implantable.

Figure 6:
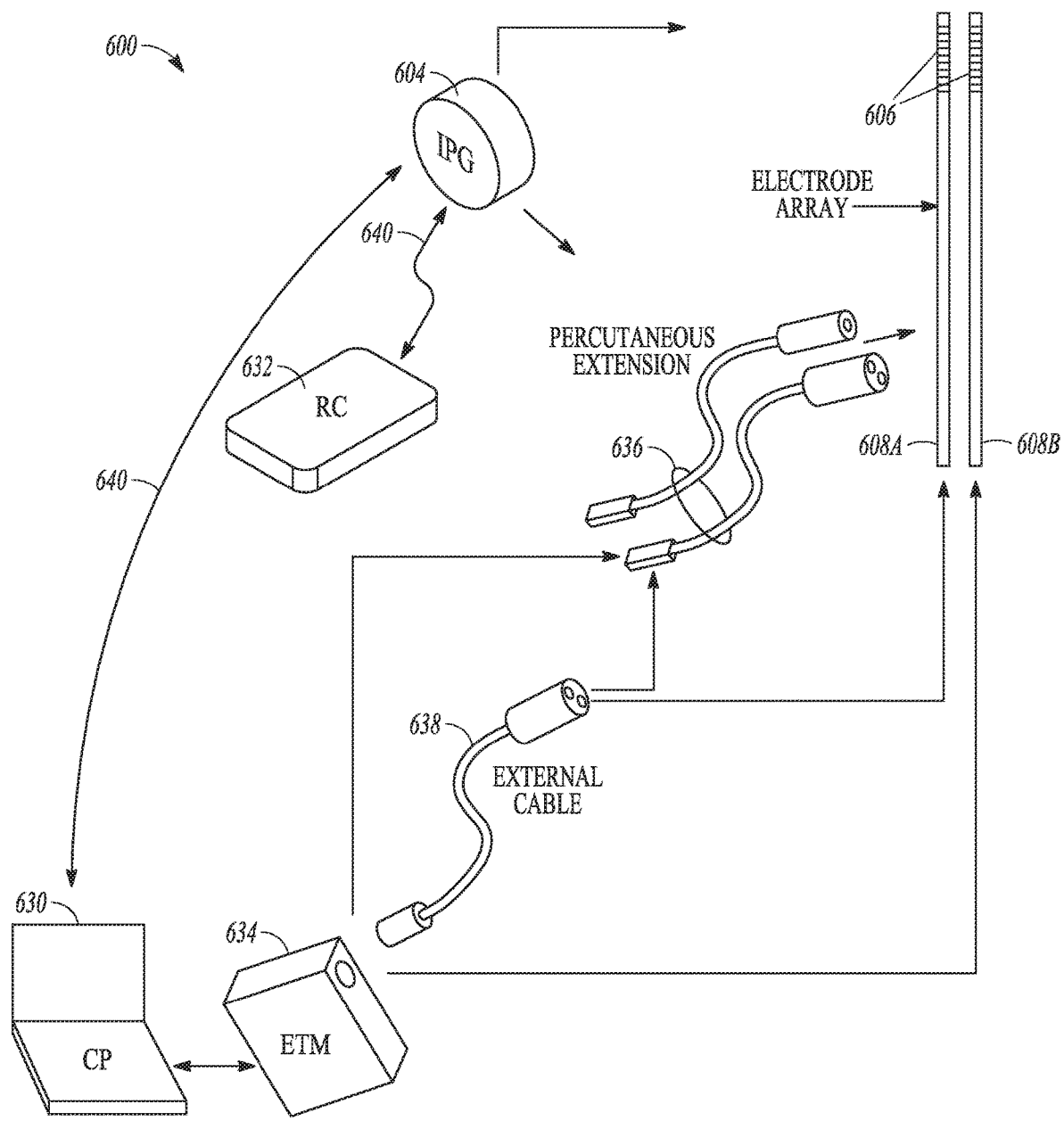
FIG. 6 illustrates an embodiment of portions of a neurostimulation system, such as the neurostimulation system of FIG. 1.

FIG. 6 illustrates an embodiment of portions of a neurostimulation system 600 as an example of portions of system 100 including programming device 102, stimulation device 104, electrodes 106. System 600 includes an IPG 604, implantable neurostimulation leads 608A and 608B, an external remote controller (RC) 632, a clinician's programmer (CP) 630, and an external trial stimulator (ETS) 634. IPG 404 may be electrically coupled to leads 608A and 608B directly or through percutaneous or paddle extension leads 636. EIS 634 may be electrically connectable to leads 608A and 608B via one or both of percutaneous or paddle extension leads 636 and/or external cable 638. System 600 can represent an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it may be more easily configurable than IPG 604.

CP 630 can configure the neurostimulation provided by ETS 634. If EIS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
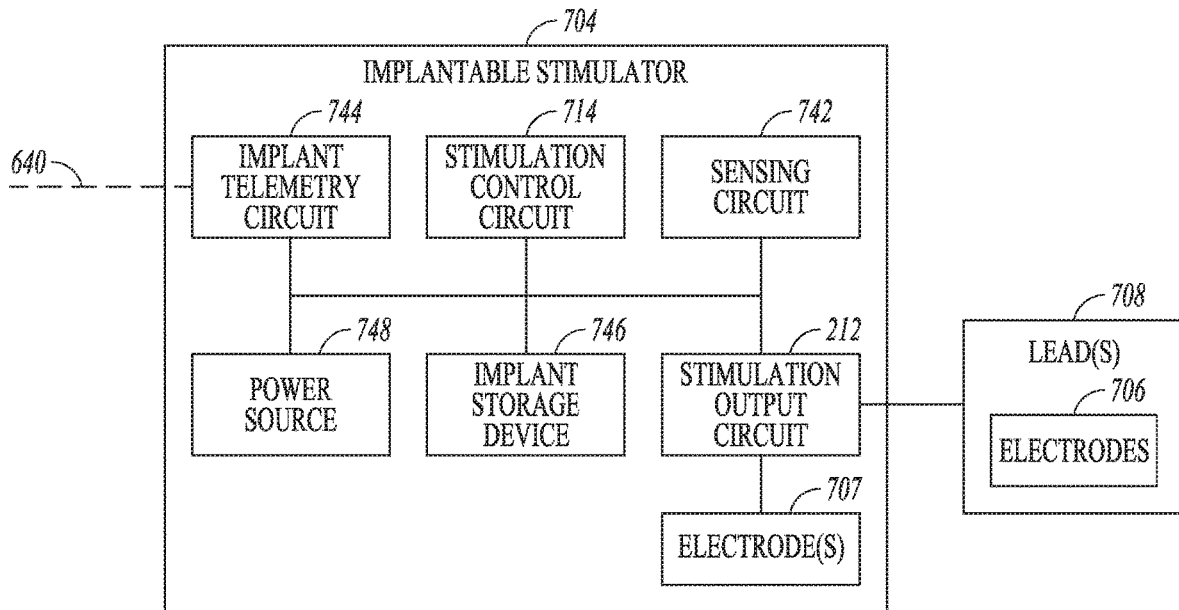
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 can represent an example of stimulation device 104 or 204 and may be implemented, for example, as IPG 404. Lead(s) 708 can represent an example of lead system 208 and may be implemented, for example, as implantable leads 408A and 408B. Lead(s) 708 includes electrodes 706, which can represent an example of electrodes 106 or 206 and may be implemented as electrodes 406.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707, and delivers each of the neurostimulation pulses through a set of electrodes selected from electrodes 706 and electrode(s) 707. Stimulation control circuit 714 can represent an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 stores one or more stimulation programs and values of the plurality of stimulation parameters for each of the one or more stimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640, and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (e.g., using micro-electrode recording, accelerometers, and/or other sensors), and/or any other information considered important or useful for providing adequate care for the patient (e.g., the patient's disease state, sensor readings, and/or pain ratings). In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
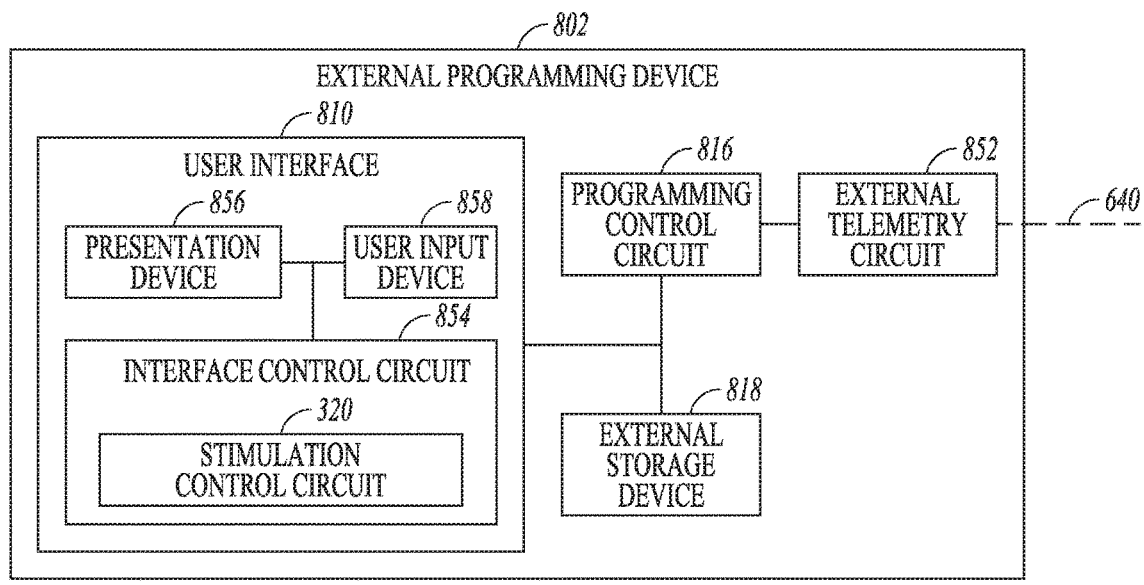
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 can represent an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). External telemetry circuit 852 and implant telemetry circuit 744 each include an antenna and RF circuitry configured to support such wireless telemetry.

External storage device 818 stores instructions for operating external programming device 802 and one or more stimulation waveforms for delivery during a neurostimulation therapy session, as well as various parameters and building blocks for defining the one or more stimulation waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steeling a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 can represent an example of programming control circuit 316 and generates the plurality of stimulation parameters, which is to be transmitted to implantable stimulator 704, based on a specified stimulation program (e.g., the pattern of neurostimulation pulses as represented by one or more stimulation waveforms and one or more stimulation fields, or at least certain aspects of the pattern). The stimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 can represent an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms, and transmits the plurality of stimulation parameters with the updated values to implantable stimulator 704.

Figure 9:
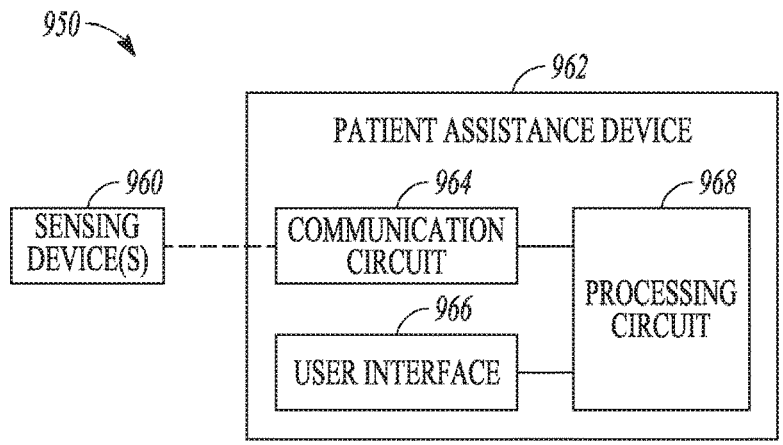
FIG. 9 illustrates an embodiment of a device management system of a neurostimulation system, such as the neurostimulation system of FIG. 1.

FIG. 9 illustrates an embodiment of a device management system 950 of a neurostimulation system, such as system 100. Device management system 950 represents an example of device management system 150 and can be configured for managing use of a stimulation device, such as stimulation device 104 including its various examples, for delivering neurostimulation to the patient. Device management system 950 can include one or more sensing devices 960 and a patient assistance device 962. Sensing device(s) 960 can sense one or more signals from the patient, and can include at least one or more non-invasive sensing devices configured to be worn by the patient (referred to as wearable sensing devices or wearable sensors). Patient assistance device 962 can assist the patient in use of the stimulation device, and can include a communication circuit 964, a user interface 966, and a processing circuit 968. Communication circuit 964 can receive the sensed one or more signals from the one or more sensing devices. User interface 966 allows for interactions between the patient assistance device and the patient. Processing circuit 968 can receive patient-specific information including the one or more signals sensed by sensing device(s) 960, analyze the received patient-specific information with neurostimulation algorithm information representative of available therapeutic options using the stimulation device, produce one or more recommendations related to use of the stimulation device for treating the patient based on one or more outcomes of the analysis, and present at least one recommendation of the produced one or more recommendations to the patient using user interface 966. The presented recommendation may indicate whether the use of the stimulation device is recommended for treating the patient and the specific neurostimulation therapy modalities recommended for that patient under various conditions, situations, and/or times of day.

Processing circuit 968 is illustrated as part of patient assistance device 962 by way of example, and not by way of restriction. In various embodiments, processing circuit 968, including its various embodiments as discussed in this document, can be located in patient assistance device 962 and/or one or more devices communicatively coupled to patient assistance device 962. In other words, a processing circuit of patient assistance device 962, including its various embodiments as discussed in this document, and/or one or more other devices, can be programmed to perform the functions of processing circuit 968, including its various embodiments as discussed in this document. Such one or more other devices can be part of a neurostimulation network that is discussed below.

In various embodiments, circuits of neurostimulation 100, including but not limited to its various embodiments discussed in this document, may be implemented using a combination of hardware and software. For example, the circuit of user interface 110, stimulation control circuit 214, programming control circuit 316, stimulation control circuit 320, communication circuit 964, user interface 966, and processing circuit 968, including but not limited to their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 10:
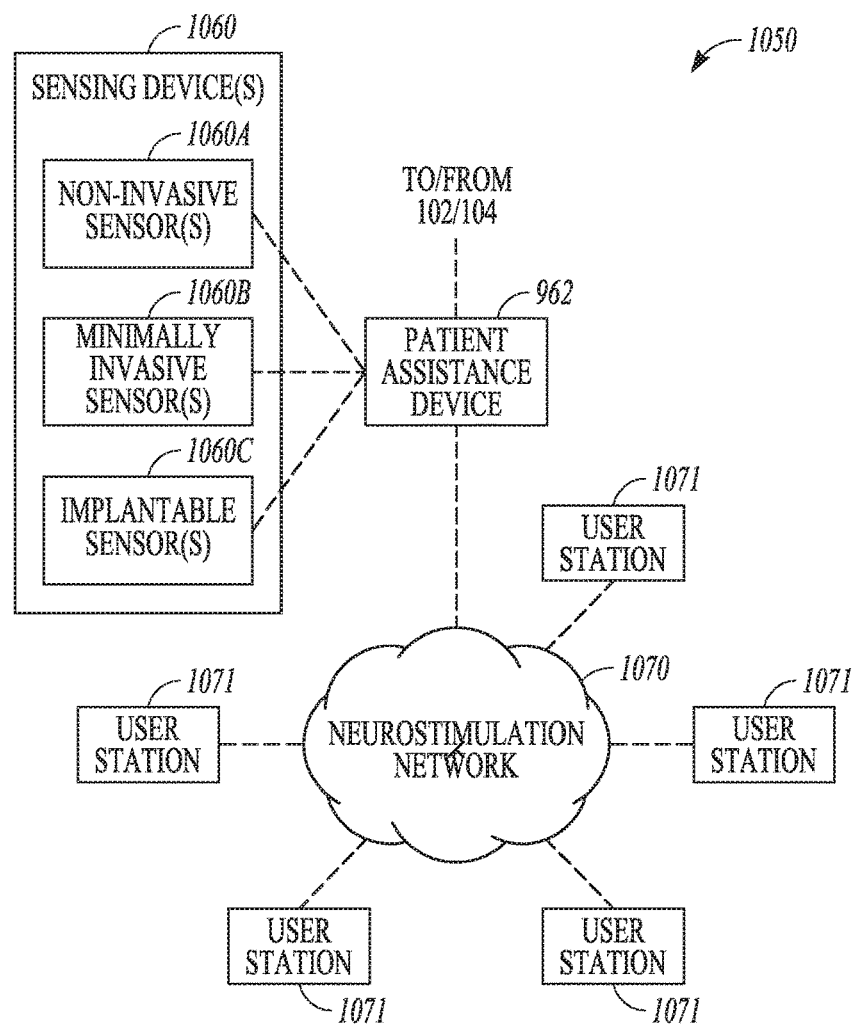
FIG. 10 illustrates a further embodiment of the device management system of FIG. 9.

FIG. 10 illustrates an embodiment of a device management system 1050, which is a further embodiment of device management system 950 and represents another example of device management system 150. Device management system 1050 can include one or more sensing devices 1060, patient assistance device 962, a neurostimulation network 1070, and user stations 1071.

Sensing device(s) 1060 can include one or more non-invasive sensors 1060A, one or more minimally invasive sensors 1060B, and/or one or more implantable sensors 1060C. In various embodiments, sensing device(s) 1060 can include any one or any combination of non-invasive sensor(s) 1060A, minimally invasive sensor(s) 1060B, and/or implantable sensor(s) 1060C. Sensing device(s) 1060 can sense one or more physiological signals from the patient. In various embodiments, sensing device(s) 1060 can also sense one or more other signals indicative of the patient's environment, physical activities, and/or other factors related to the neurostimulation. In various embodiments, the one or more physiological signals can include one or more signals providing for an objective measure of a condition of the patient indicated for or treated by the neurostimulation, such as pain.

Non-invasive sensor(s) 1060A can include one or more wearable sensor devices configured to be worn by the patient to sense one or more signals from the patient. For example, such wearable sensors can be used to sense one or more signals providing for an objective measure of pain, such as discussed in U.S. patent application Ser. No. 15/867,801, "PAIN MANAGEMENT BASED ON BRAIN ACTIVITY MONITORING", filed on Jan. 11, 2018 and U.S. patent application Ser. No. 15/888,808, "METHOD ANT) APPARATUS FOR PAIN MANAGEMENT WITH SLEEP DETECTION," filed on Feb. 5, 2018, both assigned to Boston Scientific Neuromodulation Corporation, which are incorporated by reference in their entireties. One example for non-invasive sensor(s) 1060A includes one or more skin patches. Each skin patch can include, for example, one or more of the following:

electrodes and a bioelectric sensing circuit to sense one or more bioelectric signals such as electrocardiogram (ECG), electromyogram (EMG), electroencephalography (EEG), or signals indicative of galvanic skin resistance (GSR);

a thermistor including a temperature sensor and a detection circuit to detect body temperature;

an optical sensor, such as a photoplethysmographic (PPG) sensor to sense PPG, and a detection circuit to detect heart rate, blood oxygen saturation, blood pressure, etc.; and an accelerometer and/or a gyroscope to detect motion and orientation.

In one example, a cardiac monitoring patch can record ECG for hours to weeks, e.g., 1-14 days, as prescribed by a clinician. Another example for non-invasive sensor(s) 1060A includes wrist-worn sensing device, such as a smart watch including sensors. The wrist-worn sensing device can include, for example, one or more of the following:

a PPG sensor to sense PPG, and a detection circuit to detect heart rate, blood oxygen saturation, blood pressure, etc.;

an accelerometer to detect motion and orientation;

electrodes and a bioelectric sensing circuit to sense one or more bioelectric signals such as ECG, EMG, or galvanic skin resistance;

a location sensor, such as based on the global positioning system (GPS);

a microphone;

a thermistor; and a worn-detection sensor to detect whether the smart watch is being worn.

Minimally invasive sensor(s) 1060B can be worn by the patient to sense one or more signals for which no suitable non-invasive sensor is available. Examples of minimally invasive sensor(s) include EMG, body temperature, ECG, and sensors. Implantable sensor(s) 1060C can be implanted in the patient to sense one or more signals. Examples of implantable sensors include a cardiac implantable loop recorder (ILR), a nerve cuff electrode to record neural signals, and a blood pressure sensor. In various embodiments, selection of sensors can depend on the signals that need to be sensed, types of sensor suitable for sensing the needed signals, and ease of use for the user and/or the patient. For example, non-invasive sensor(s) 1060A may be preferred for evaluating the patient when no device has been implanted into the patient, while implantable sensor(s) 1060C may be preferred when an implantable stimulation device is used and one or more sensors can be incorporated into the implantable stimulation device and/or easily connected to the implantable stimulation device within the patient's body. In various embodiments, when an implantable stimulation device is used, implantable sensor(s) can be included in and/or communicatively coupled to the implanted stimulation device, and non-invasive and/or minimally invasive sensor(s) can be communicatively coupled to the implanted stimulation device.

Neurostimulation network 1070 allows many users to participate in treatment of the patient using system 100, including its various embodiments. User stations 1071 can each be a computer, smartphone, or other device configured to be communicatively coupled to neurostimulation network 1070 and used by various types of users to access to neurostimulation network 1070. FIG. 10 shows five user stations for the purpose of illustration rather than limitation, in various embodiment, neurostimulation network 1070 is an Internet (cloud) based system.

Figure 11:
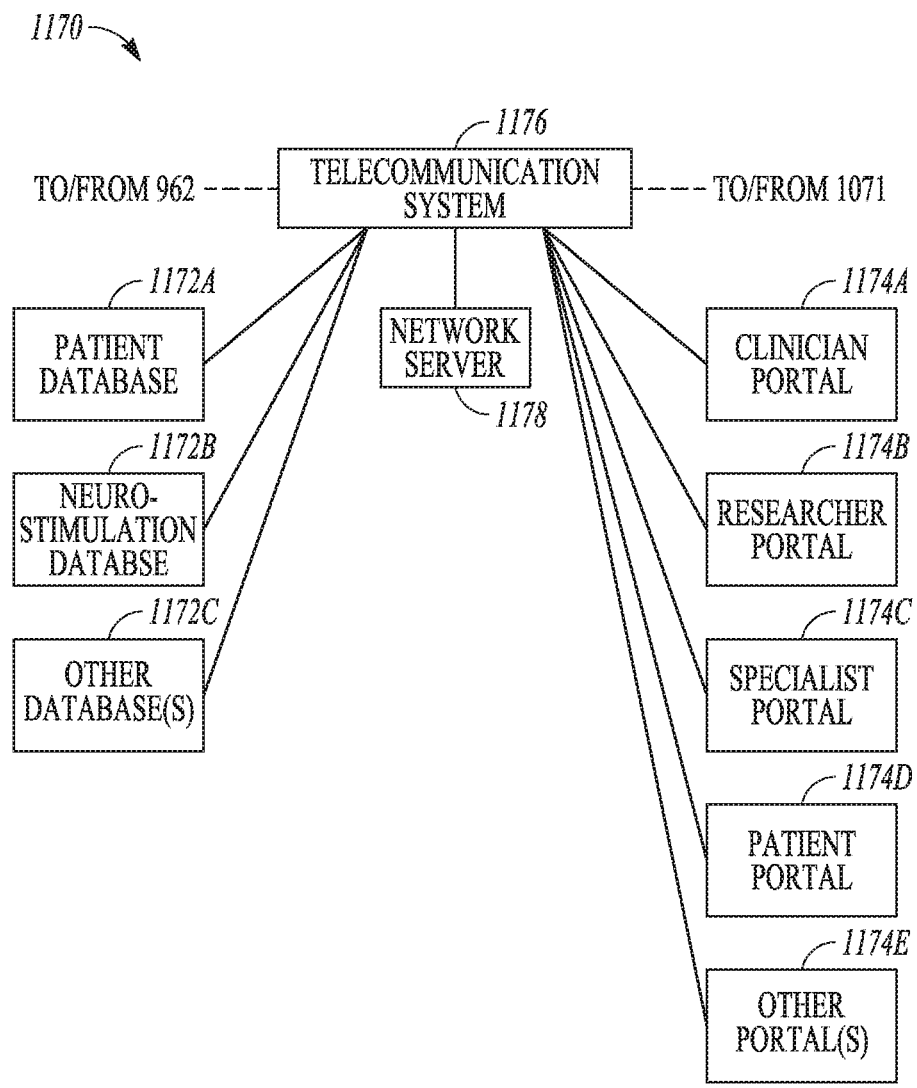
FIG. 11 illustrates an embodiment of a neurostimulation network of a device management system, such as the device management system of FIG. 9.

FIG. 11 illustrates an embodiment of a neurostimulation network 1170, which represents an example of neurostimulation network 1070 and allows various types of users to participate in treatment of the patient using system 100, including its various embodiments, Examples of the users can include:

clinicians, such as physicians or other care providers authorized to prescribe the neurostimulation for the patient;

researchers, such as scientists and engineers developing neuromodulation therapy algorithms and parameters;

device specialists, such as specialists trained to program the stimulation device and maintain operation of the stimulation device, including device provider's clinical representatives and technical support personnel;

specialists with expertise in one or more aspects of the stimulation device.

Neurostimulation network 1170 can include databases 1172, web portals 1174, a telecommunication system 1176, and a network server 1178. The web portals each allow the patient or a type of the users to access to designated resources available in or through neurostimulation network 1170 using user stations 1070. Telecommunication system 1176 provides for connections among data bases 1172, web portals 1174, and user stations 1070. Network server 1178 can manage access to the databases and web portals through web portals 1174.

In various embodiments, data bases 1172 can include a patient database 1172A, a neuromodulation database 1172B, and optionally one or more other data bases 1172C. Patent database 1172A can include an electronic medical record (EMR) or electronic health record (EHR) system, and can include portions of the patient-specific information. Neurostimulation algorithm database 1172B can include various stimulation programs for one or more therapies. Multiple stimulation programs can be stored for one therapy. For example, for an SCS therapy, different stimulation programs are stored for use when the patient is sleep, awake and active, awake and sedentary, walk, run, etc., to be selected based on detection of physical activity state of the patient and/or time of day. Different stimulation programs can also be provided for different modalities, e.g., supra-perception, sub-perception, sharp pain, throbbing pain, etc. Other databases 1172C can include any other information useful in managing neurostimulation and/or other therapies for the patient.

In various embodiments, web portals 1174 can include a clinician portal 1174A, a researcher portal 1174B, a specialist portal 1174C, a patient portal 1174D, and optionally one or more other portals 1174E. Clinician portal 1174A can allow for access to neurostimulation network 1170 by one or more clinicians using one or more of user stations 1071. This can allow the one or more clinician to determine whether the patient should receive the neurostimulation and to control the delivery of the neurostimulation to an extent corresponding to responsibility of the one or more clinicians to the patient. Researcher portal 1174B can allow for access to neurostimulation network 1170 by one or more researchers using one or more of user stations 1071. This can allow the one or more researchers to participate in the further development of neurostimulation technology based on feedback from the patient and/or other users, such as by modifying and/or creating stimulation programs. Specialist portal 1174B can allow for access to neurostimulation network 1170 by one or more device specialists using one or more of user stations 1071. This can allow for control of operation of the stimulation device, and trouble-shooting when needed, for example by the device provider's clinical representatives and technical support personnel. Patient portal 1174D can allow for access to neurostimulation network 1170 by the patient using patient assistance device 962 and/or an authorized device of user stations 1071. This can assist the patient with patient-control of the neurostimulation. Other portal(s) 1174E can allow for access to neurostimulation network 1170 by one or more other authorized persons using one or more of user stations 1071. In various embodiments, neurostimulation network 1170 can provide a platform for various types of the users or other persons related to neurostimulation to participate in optimization the delivery of the neurostimulation for the patient and/or collaborate in development of neurostimulation technology.

Figure 12:
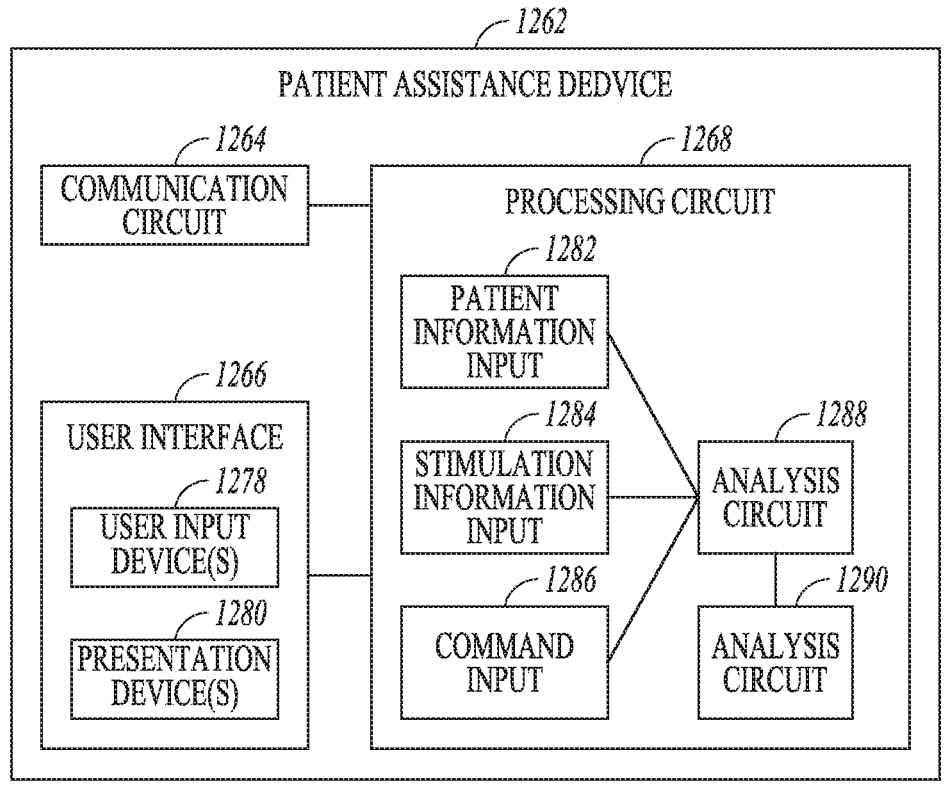
FIG. 12 illustrates an embodiment of a patient assistance device of a device management system, such as the device management system of FIG. 9.

FIG. 12 illustrates an embodiment of a patient assistance device 1262, which represents an example of patient assistance device 962 and provides the patient with assistance in use of a stimulation device such as stimulation device 104, including its various embodiments. In various embodiments, patient assistance device 962 can include a mobile device. For example, patient assistance device 962 can be implemented by configuring a generic mobile device, such as a smartphone. Alternatively, patient assistance device 962 can be implemented as a specialized mobile device. If the patient does not use a mobile device for any reason, patient assistance device 962 can be implemented, for example, in a desktop computer or as a specialized desktop device. In one embodiment, patient assistance device 1262 can include RC 632. For example, patient assistance device 1262 and RC 632 can be integrated into a specialized hand-held device. Alternatively, a generic device, such as a smartphone, can be programmed to performed functions of patient assistance device 1262 and RC 632.

Patient assistance device 1262 can include a communication circuit 1264, a user interface 1266, and a processing circuit 1268. Communication circuit 1264 can be an example of communication circuit 964, and can support communication between patient assistance device 1268 and each of one or more sensing devices 1060, neuromodulation network 1070, RC 632, stimulation device 104 (if RC 632 not used), and of CP 630 (including various embodiments of these system components).

User interface 1266 can be an example of user interface 966, can allow for interactions between patient assistance device 1262 and the patient, and can include one or more user input devices 1278 to receive input from the patient and one or more presentation devices 1280 to present information to the patient. User input device(s) 1278 can include any types of user input devices that can support the various functions of patient assistance device 1262, such as touch-screen, buttons, keyboard, keypad, touchpad, trackball, joystick, and/or mouse. Presentation device(s) 1280 can include any type of presentation device that can convey the information as discussed in this document to the patient, such as a non-interactive screen, a touchscreen, light-emitting diode(s), and speaker(s). In embodiments in which patient assistance device 1262 is implemented in a smartphone, user interface 1266 is that of the smartphone.

Processing circuit 1268 can be an example of processing circuit 968, and can include a patient information input 1282, a stimulation information input 1284, a command input 1286, an analysis circuit 1288, and an output circuit 1290. Patient information input 1282 can receive the patient-specific information indicative of conditions of the patient. Such conditions can include physical, physiological, and any other conditions related to determination of whether and how to treat the patient using neurostimulation. The patient-specific information can include the one or more signals sensed by sensing device(s) 1060, information received from neurostimulation network 1070, and information received from the patient through user interface 1266. Stimulation information input 1284 can receive neurostimulation algorithm information representative of available therapeutic options, such as from neurostimulation network 1070. Command input 1286 can receive user commands, such as commands entered by the patient using user input device(s) 1278 and/or commands entered by an authorized user through neurostimulation network 1070. The user command can control, for example, the process determining whether and how to treat the patient using neurostimulation. Analysis circuit 1288 can analyze at least the received patient-specific information and produce one or more recommendations related to use of the stimulation device in treating the patient based on one or more outcomes of the analysis. In various embodiments, analysis circuit 1288 can analyze the received patient-specific information and the received neurostimulation algorithm information to produce one or more recommendations. In various embodiments, analysis circuit 1288 can analyze the received patient-specific information, the received neurostimulation algorithm information, and the received user commands to produce one or more recommendations. The one or more commands can include at least a recommendation regarding whether to use the stimulation device to treat the patient (e.g., whether to implant IPG 604 into the patient. In various embodiments, the one or more recommendations can include whether to use the stimulation device to treat the patient, initial settings of the stimulation device, and/or adjustments to the settings of the stimulation device. Output circuit 1290 can route each of the one or more recommendations to presentation device(s) 1280 and/or communication circuit communication circuit 1264, to convey the one or more recommendations to the patient and/or the user.

Processing circuit 1268 is illustrated as part of patient assistance device 1262 by way of example, and not by way of restriction. In various embodiments, processing circuit 1268 can be implemented in either or both of patient assistance device 1262 and neurostimulation network 1070 or 1170. In other words, patient assistance device 1262 and/or one or more other devices in neurostimulation network 1070 or 1170 can be programmed to perform the functions of processing circuit 1268, in any manner deemed suitable as determined by those skilled in the art.

Figure 13:
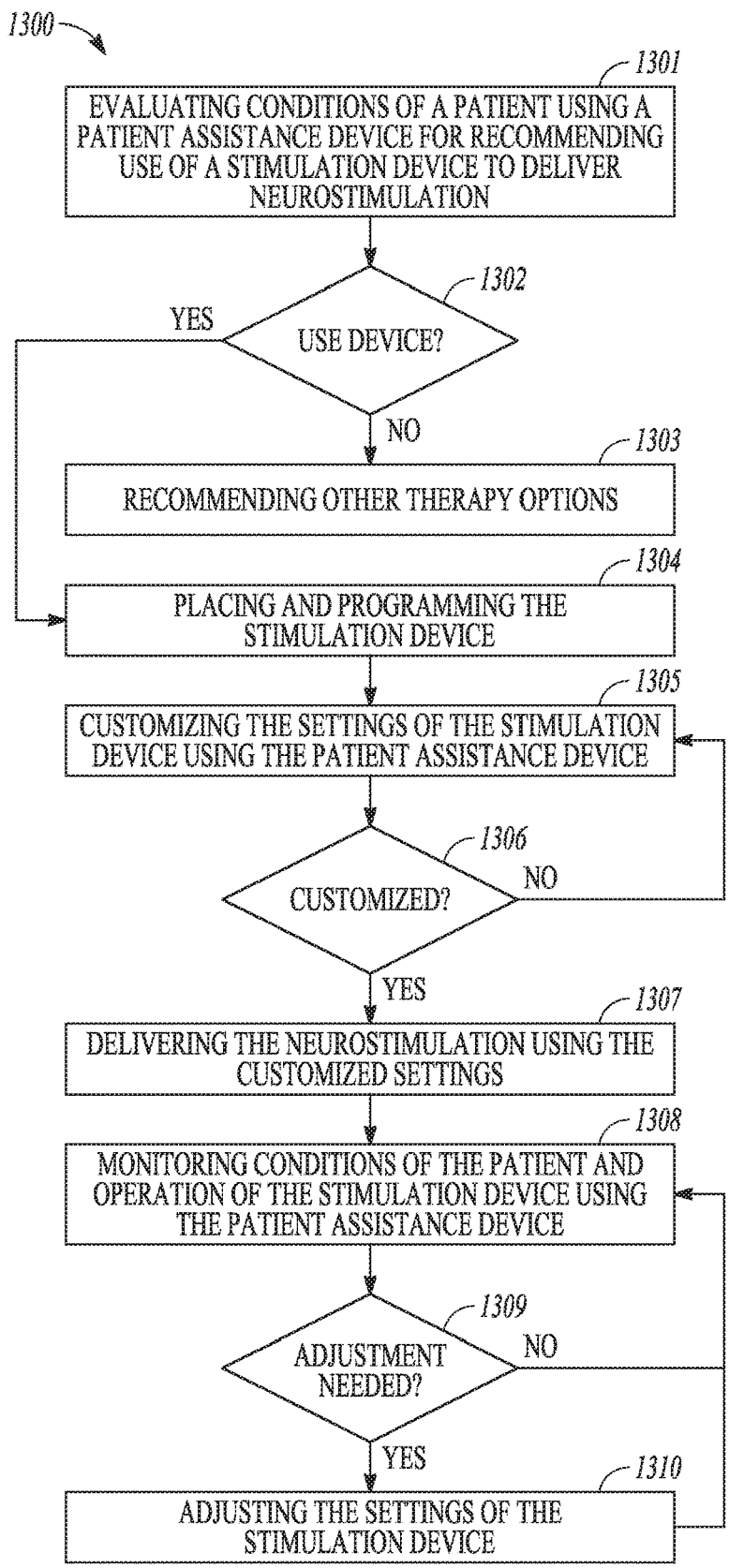
FIG. 13 illustrates an embodiment of a method for managing use of a stimulation device for treating a patient using neurostimulation.

FIG. 13 illustrates an embodiment of a method 1300 for managing use of a stimulation device for treating a patient using neurostimulation. In one embodiment, a patient assistance device such as patient assistance device 962 or 1262, which has a processing circuit such as processing circuit 968 or 1268, is configured to perform method 1300. Instructions for performing method 1300 and/or any other functions discussed in this document can be stored, for example, in a memory device of patient assistance device 962 or 1262. In the following discussion with references to FIGS. 13-16, a "patient assistance device" can include, but is not limited to, patient assistance device 962 or 1262, a "processing circuit" can include, but it not limited to, processing circuit 968 or 1268, and a "stimulation device" can include, but it not limited to, stimulation device 104 or 204, IPG 604, or implantable stimulator 704. In one embodiment, the processing circuit can have multiple operation modes and operated in an operation mode selected based on the stage of use of a stimulation device, as discussed below. The mode of operation can be selected automatically (e.g., based on stage of usage of the stimulation device) and/or a user command received by the patient assistance device. It is to be understood that method 1300 is not limited to being performed by any particular structures such as those discussed in this document. For example, various functions may be performed using the patient assistance device alone or performed using the patient assistance device and/or other devices within and/or connected through a network such as neurostimulation network 1070.

At 1301, conditions of a patient are evaluated using a patient assistance device for recommending use of a stimulation device to deliver neurostimulation to the patient. The processing circuit can operate in an evaluation mode for evaluating the conditions of the patient to predict an outcome of the neurostimulation for the patient. One or more recommendations can be produced based on the predicted outcome, such as whether to use the stimulation device and, if the stimulation device is to be used, initial settings of the stimulation device (e.g., one or more stimulation programs and parameters used for each stimulation program) and conditions under which a particular set of settings could be used (e.g., when the patient is sleeping, walking, or exercising).

If the use of the stimulation device is not recommended at 1302, other therapy options may be recommended at 1303. This may include directing the patient to contact a particular physician, other care provider, or healthcare facility, or suggesting concomitant therapies (e.g., physical therapy, biofeedback, massage, and/or yoga). If the use of the stimulation device is recommended at 1302, the stimulation device is placing in, on, or about the patient, and programmed for delivering the neurostimulation to the patient at 1304. In one embodiment, the stimulation device includes an implantable device such as IPG 604, which is to be implanted into the patient at 1304. The programming is performed by a device specialist such as a clinical representative of the device provider using a programmer such as CP 630.

At 1305, the settings of the stimulation device are customized for the patient using the patient assistance device. The processing circuit can be switched to operate in a customization mode for customizing the settings of the stimulation device for the patient after the stimulation device is programmed with the initial settings. The customization can be a process that begins after delivery of the neurostimulation from the stimulation device to the patient has started. In various embodiments, the settings of the stimulation device are optimized for the patient.

If the settings of the stimulation device are not customized at 1305, the customization process at 1305 continues. The customization is completed when the patient and/or the user responsible for the process accept the settings. When the customization includes optimization of the settings of the stimulation device with one or more target measures of performance, the settings are considered optimized when the settings are accepted by the patient and/or the user. If the settings of the stimulation device are customized (i.e., the customization is completed) at 1305, the neurostimulation is delivered to the patient from the stimulation device using the customized settings at 1307.

At 1308, conditions of the patient and operation of the stimulation device are monitored using the patient assistance device. The processing circuit can be switched to operate in a monitoring mode for monitoring conditions of the patient and operation of the stimulation device after the settings of the stimulation device are customized for the patient. The settings of the stimulation device can be adjusted based on changes in the conditions of the patient and operation of the stimulation device. In various embodiments, the settings of the stimulation device can be adjusted to re-optimize the settings of the stimulation device in response to detected changes in the condition of the patient, to respond to requests of the patient for help, and/or to detect need and information for trouble-shooting. The network such as neurostimulation network 1070 allows the settings of the stimulation device to be adjusted remotely when needed. This eliminates the need for the patient to go to a care provider's office or other specialized facilities for various adjustments of the stimulation device.

If a need for adjusting the settings of the stimulation device is not detected at 1309, the monitoring process at 1308 continues. If the need for adjusting the settings of the stimulation device is detected at 1309, the settings of the stimulation device are adjusted at 1310. Then, the monitoring process at 1308 continues.

In various embodiments, whether a new firmware update or upgrade for the stimulations device is checked using the patient assistance device at 1308, as part of monitoring the operation of the stimulation device. At 1309, whether the firmware should be updated or upgraded is recommended, such as based on potential benefits to the patient as determined by the patient assistance device. If the update or upgrade is recommended at 1309, the new firmware is installed in the stimulation device at 1310. If the update or upgrade is not recommended at 1309, the monitoring process at 1308 continues.

Figure 14:
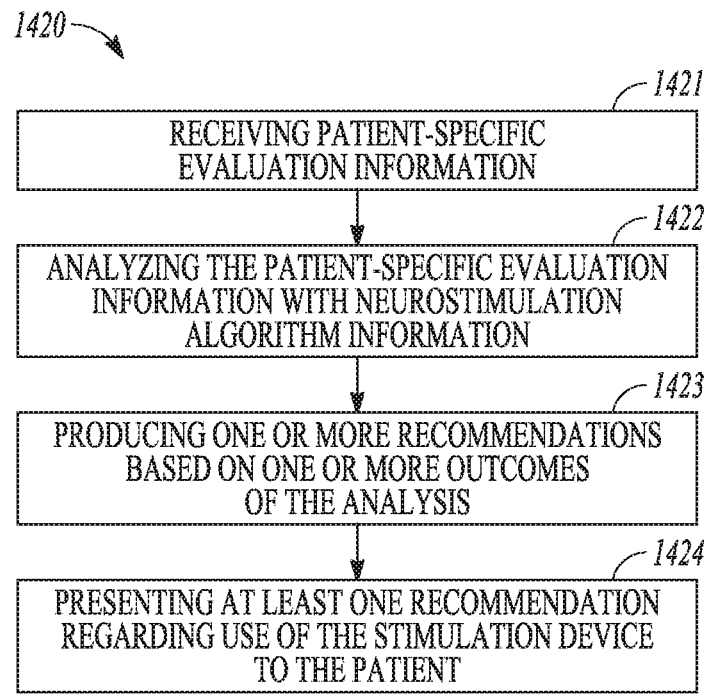
FIG. 14 illustrates an embodiment of a method for evaluating the patient for neurostimulation, such as performed as part of the method of FIG. 13.

FIG. 14 illustrates an embodiment of a method 1420 for evaluating the patient for neurostimulation. Method 1420 can be performed during step 1301 in method 1300. In one embodiment, the processing circuit of the patient assistance device operates in the evaluation mode to perform method 1420.

At 1421, patient-specific evaluation information is received by the processing circuit of the patient assistance device. The patient-specific evaluation information includes portions of the patient-specific information that are received by the patient assistance device and analyzed as part of performing method 1420 (e.g., during the evaluation mode). The patient-specific evaluation information can include input from the patient. For example, a questionnaire can be presented to the patient, and answers can be received from the patient, using a user interface of the patient assistance device. This is to obtain information that is subjective in nature, is not obtainable using other manner, and/or needs verification by the patient. Examples of such information include pain logs capturing the patient's perception of pain, mood logs that capture the patient's mental status, answers to contextual questions for verifying or clarifying events detected by the sensors (e.g., verification of a detected fall and description of the fall and changes in pain that may be caused by the fall). Answers to the questions can be received in a variety of formats, such as multiple choice, free text, and voice recording, and can depend on nature of the question. The patient-specific evaluation information can also include one or more physiological and/or other signals sensed by one or more sensing devices such as sensing device(s) 1060. When needed, the patient assistance device can present instructions for the patient to perform certain tasks (e.g., walking for 5 minutes, or performing a specified set of activities) before recording the received one or more sensed physiological and/or other signals. The patient-specific evaluation information can further include information stored in a patient database such as patient database 1172A. Examples of such stored information include imaging data (x-ray, CT, MRI), genomic information, medical history, and standard assessments (written or physical) collected for the patient.

At 1422, the patient-specific evaluation information is analyzed with neurostimulation algorithm information. The neurostimulation algorithm information can include information representing therapeutic options available for delivery using the stimulation device. Examples of such neurostimulation algorithm information include stimulation programs and parameters used for each of the stimulation programs. The neurostimulation algorithm information can also include information such as computational models that relate the stimulation programs and parameters to possible conditions of the patient and allow for prediction of outcome of delivering the neurostimulation by simulations.

At 1423, one or more recommendations are produced based on one or more outcomes of the analysis. Outcome of the neuromodulation can be predicted by analyzing the received patient-specific information with the neurostimulation algorithm information (e.g., using simulations with the computational models). The prediction can serve as basis for the one or more recommendations. The one or more recommendations can include a recommendation for using the stimulation device, and can further include a recommendation for the initial settings of the stimulation device. The recommendation for the initial settings of the stimulation device can include, for example, selection of a type or model of the stimulation device, selection of one or more stimulation programs from the neurostimulation algorithm information, values of parameters for each selected stimulation program. Examples of such parameters may include parameters specifying waveforms of the neurostimulation, lead selection, electrode configuration (e.g., selection and fractionalization) and location in the patient. The recommendation for the initial settings of the stimulation device can also include length of trial for each selected stimulation program and order of selected stimulation programs (if more than one selected) for the trial (based on predicted likeliness of success). The recommended initial settings of the stimulation device can be provided to the user as a set of patient-specific programming scripts that the user (e.g., a clinical representative of the device provider) can tailor to the patient during programming the stimulation device using a programming device such as CP 630.

At 1424, at least one recommendation regarding use of the stimulation device is presented to the patient using the patient assistance device. The recommendation can inform the patient with therapeutic options and/or instruct the patient on how to proceed based on the prediction made at 1423. The prediction and/or the one or more recommendation can also be transmitted to the users (e.g., through a network such as neurostimulation network 1070). Some recommendations, such as the initial settings of the stimulation device, may only be presented to designed user(s). The one or more recommendations can be transmitted to a clinician (e.g., to clinician portal 1174A) to be used for applying for insurance pre-authorization and for prescribing one or more therapies, among other things. The one or more recommendations can also be used by the clinician to determine whether the patient should go through a short-term trial with a temporary stimulation device or directly receive permanent implantation of an implantable stimulator such as IPG 604 (e.g., when the prediction clearly indicates efficacy). The one or more recommendations can also be transmitted to one or more participating researchers (e.g., to researcher portal 1174B) to be used for creating and/or modifying stimulation programs and/or parameters). The one or more recommendations can also be transmitted to a device specialist such as a clinical representative of the device provider (e.g., to specialist portal 1174C) to be used for programming the stimulation device. In various embodiments, comments on the one or more recommendations are received by the patient assistance device from the patient and through the network from the users and communicated among the users for determining a therapy plan for the patient.

Figure 15:
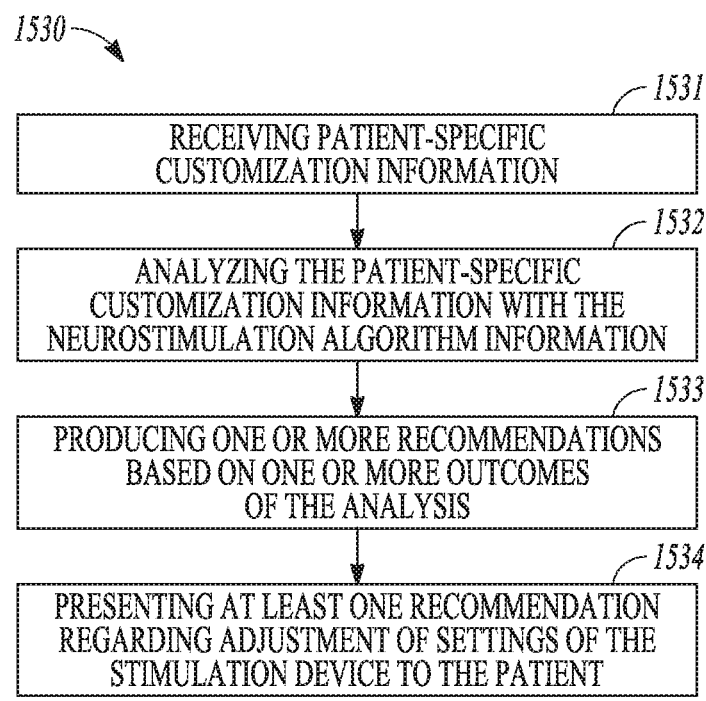
FIG. 15 illustrates an embodiment of a method for customizing settings of a stimulation device for the patient, such as performed as part of the method of FIG. 13.

FIG. 15 illustrates an embodiment of a method 1530 for customizing settings of the stimulation device for the patient. Method 1530 can be performed during step 1305 of method 1300. In one embodiment, the processing circuit of the patient assistance device operates in the customization mode to perform method 1530.

At 1531, patient-specific customization information is received by the processing circuit of the patient assistance device. The patient-specific customization information includes portions of the patient-specific information that are received by the patient assistance device and analyzed as part of performing method 1530 (e.g., during the customization mode). The patient-specific customization information can include information received from the patient in the same manner as in step 1421. The patient-specific customization information can also include one or more physiological and/or other signals sensed by one or more sensing devices such as sensing device(s) 1060. If an implantable device such as IPG 604 has been implanted, one or more signals can be sensed by one or more implantable sensing devices included in and/or connected to the implantable device. The one or more physiological and/or other signals can be sensed while the neurostimulation is delivered from the implantable device or an external stimulation device such as ETS 634, such as during an implantation and initial programming procedure.

At 1532, the patient-specific customization information is analyzed with the neurostimulation algorithm information. This analysis can be similar to the analysis at step 1422. At 1533, one or more recommendations are produced based on one or more outcomes of the analysis. The one or more recommendations can include instructions for adjusting the settings of the stimulation device based on the received patient-specific customization information. Such adjustment can target on maintaining optimization of the settings of the stimulation device throughout use of the stimulation device. Examples of the one or more recommendations include instructions for switching between the stimulation programs, instructions for changing parameters used for each of the stimulation programs, instructions for changing schedule of delivering the neurostimulation (e.g., stating time for each stimulation program, such as for daytime/nighttime and/or weekday/weekend deliveries), instructions for creating an evaluation strategy/algorithm for optimizing stimulation device settings for the patient by testing the one or more stimulation programs and the parameters by delivering the stimulation using the stimulation device, and instructions for changing the settings of the stimulation device in response to changes in conditions of the patient and/or the stimulation device over time to increase longevity of the stimulation device. Each of such one or more recommendations may be intended for the patient or one or more designated users, depending on the nature of the recommendation.

At 1534, at least one recommendation regarding adjustment of settings of the stimulation device is presented to the patient using the user interface of the patient assistance device. This recommendation can include instructions for the adjustment that can be followed by the patient. When a recommended adjustment needs to be reviewed by a clinician, the recommendation can be transmitted to the clinician (e.g. to clinician portal 1174A) for obtaining approval from the clinical. If approved, the recommendation is presented to the patient. The patient's response to at least some types of recommendations can be received using the user interface of the patient assistance device. Examples of such responses include a response indicating no adjustment as chosen by the patient (e.g., when the patient feels no such need) and a response indicating that the adjustment is performed (i.e., as recommended). If the patient assistance device is capable of communicating with the stimulation device directly, programming instructions can be transmitted to the stimulation device for adjusting its settings of the stimulation device based on the response received from the patient. If the patient assistance device is capable of communicating with the stimulation device by communicating with a patient programming device such as RC 632 directly (i.e., not through the patient or user), programming instructions can be transmitted through the patient programming device to the stimulation device for adjusting its settings of the stimulation device based on the response received from the patient. If the patient assistance device is not capable of communicating with either the stimulation device or the patient programming device directly, instructions are presented to the patient to adjust the stimulation device using the patient programming device such as RC 632 according to the recommendations. The patient assistance device may also present a tutorial (e.g., a video tutorial) on how to use the patient programming device such as RC 632 to adjust the stimulation device according to various recommendations.

Figure 16:
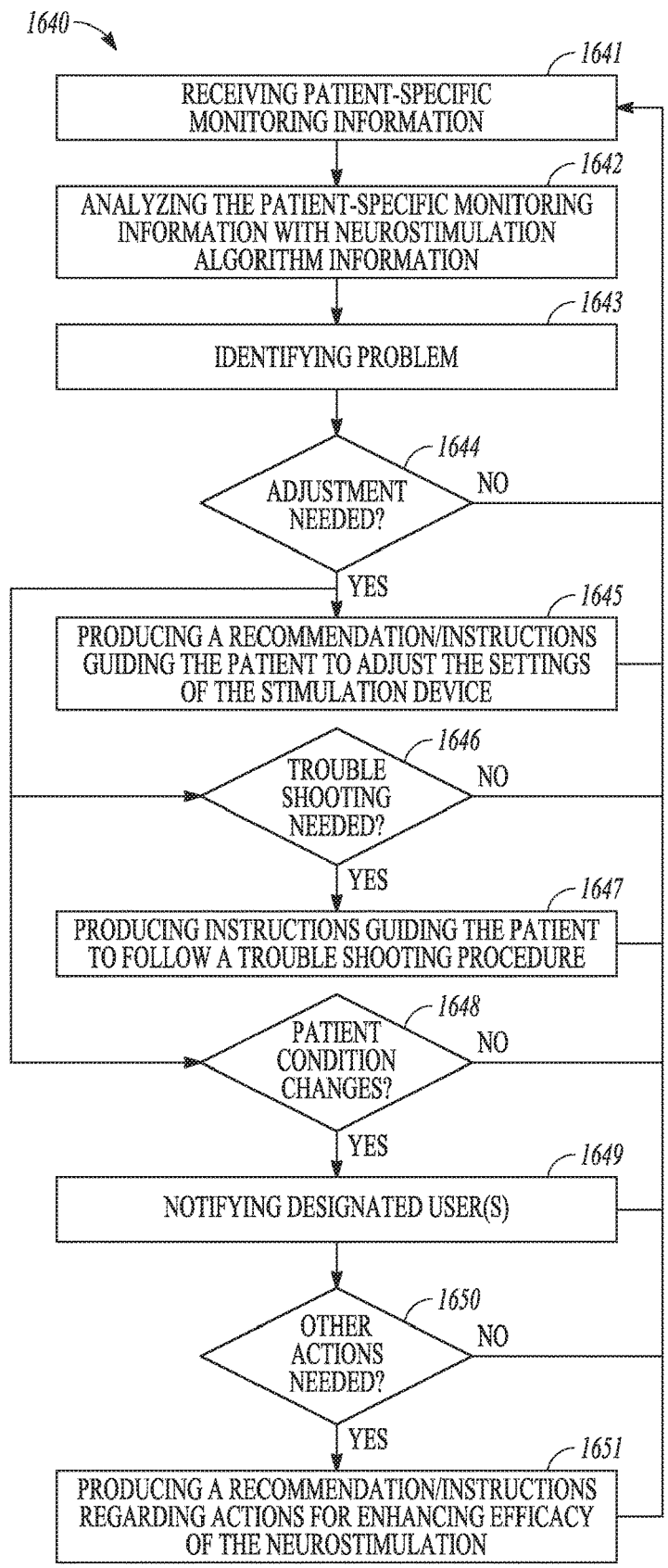
FIG. 16 illustrates an embodiment of a method for monitoring the patient during treatment using the stimulation device, such as performed as part of the method of FIG. 13.

FIG. 16 illustrates an embodiment of a method 1640 for monitoring the patient during treatment using the stimulation device. Method 1640 can be performed during steps 1308, 1309, and 1310 of method 1300. In one embodiment, the processing circuit of the patient assistance device operates in the monitoring mode to perform method 1640.

At 1641, patient-specific monitoring information is received by the processing circuit of the patient assistance device. The patient-specific monitoring information includes portions of the patient-specific information that are received by the patient assistance device and analyzed as part of performing method 1640 (e.g., during the monitoring mode). The patient-specific monitoring information can include information received from the patient in the same manner as in step 1421 or 1531. The patient-specific monitoring information can also include one or more physiological and/or other signals sensed by one or more sensing devices such as sensing device(s) 1060. If the stimulation device includes an implantable device such as IPG 604, one or more signals can be sensed by one or more implantable sensing devices included in and/or connected to the implantable device. In one embodiment, one or more physiological signals from the one or more non-invasive or minimally invasive sensing devices during an initial period, periodically, and/or as needed, while one or more (same of different) physiological signals are received from one or more implantable sensors continuously or on a regular and frequent basis. The patient-specific monitoring information can also include operation history of the stimulation device.

At 1642, the patient-specific monitoring information is analyzed with the neurostimulation algorithm information. This analysis can be similar to the analysis at step 1422 or 1532. At 1643, an outcome of the analysis is used to identify any problems. A "problem" to be identified at 1643 can include any indication of a need for adjusting the therapy being delivered to the patient, which may or may not require adjustment of the settings of the stimulation devices. Such a problem may be caused, for example, a change in the conditions of the patient, a change is the environment of the patient, a change in the daily routine (e.g., sleeping time) of the patient, a change in the status of the stimulation device (e.g., battery status), and malfunctioning of the stimulation device. The problems can be identified based on the received patient-specific monitoring information. The identification can be performed automatically (e.g., continuously, periodically, or in response to detection of an indication of a problem) and/or in response to a request made by the patient or one of the users. For example, if the patient feels the need for adjusting the therapy or checking on the stimulation device, he or she may use the patient assistance device to enter a request as a command, and/or inform a designated user. If a possible problem is observed, or a notification from the patient is received, by one of the users remotely, a command can be transmitted to the patient assistance device via the network.

If no adjustment is needed (i.e., no problem is identified) at 1644, the performance of method 1640 continues from the beginning (1641). If adjustment is needed (i.e., a problem is identified) at 1644, the performance of method 1640 continues to one of the next steps depending on the nature of the identified problem. Such next steps can include detecting a need for trouble shooting the stimulation device and detecting changes in the condition of the patients, as illustrated in FIG. 16 by way of example, but not by way of restriction.

At 1645, a recommendation guiding the patient to adjust the settings of the stimulation device is produced, if the identified problem can be corrected by the patient using the patient assistance device. The recommendation can be presented to the patient as instructions that can by followed by the patient.

If a need for trouble shooting is not identified at 1646, the performance of method 1640 continues from the beginning (1641). If a need for trouble shooting is identified at 1646 (e.g., when the identified problem cannot be addressed by adjusting the settings of the stimulation device), instructions guiding the patient to follow a trouble shooting procedure are produced at 1647. The instructions are presented to the patient. The performance of method 1640 can continue from the beginning (1641) while pending trouble shooting, but this may depend on the nature of the identified problem and whether the neurostimulation should continue to be delivered. If the patient does not follow the instructions to have the problem addressed. The instructions can be repeated as needed, and the user responsible for care of the patient can be notified of the patient's non-responsiveness. In various embodiments, the patient assistance device can identify a person suitable for addressing the detected problem based on nature of the detected problem and transmit a request to the identified person. If the patient is identified as the suitable person, the patient assistance device can produce and present instructions using the user interface for the patient to address the detected problem. If one of the users is identified as the suitable person, the patient assistance device can produce a notification and transmit the notification to the identified person using the communication circuit via the network. The patient assistance device can also be configured to allow remote troubleshooting by the identified person via the network to address the detected problem.

If no change in the patient's conditions is detected at 1648, the performance of method 1640 continues from the beginning (1641). If one or more changes in the patient's conditions are detected at 1648, one or more designated users are notified. If a need for actions in addition to notifying the one or more designated users is not detected at 1650, the performance of method 1640 can continue from the beginning (1641) while pending responses from the notified user(s). If the need for actions in addition to notifying the one or more designated users is detected at 1650, a recommendation regarding actions to be taken by the patient is produced at 1651. The recommendation can be presented as instructions for the patient to follow, such as taking medication and/or adjusting daily activities. Under various circumstances, actions may be recommended for enhancing efficacy of the neurostimulation. In various embodiments, the patient assistance device can identify changes in the conditions of the patient for follow-up, identify a need to match the patient to a different device specialist (e.g., the clinical representative of the device provider designed for care of the patient) based on the received patient-specific monitoring information, and/or identify a need to match the patient to a different clinician based on the received patient-specific information. The recommendation produced at 1651 can include such identified changes and needs. At 1651 (as well as other times when method 1640 us performed), the patient assistance device can also recommend various behaviors (e.g., activities and diets) for enhancing outcomes of the neuromodulation therapy to the patient. For example, the patient assistance device can identify complementary treatments, activities, and/or behaviors that can be combined with the neurostimulation delivered from the stimulation device. Examples of such complementary treatments, activities, and/or behaviors include additions or adjustments of medication, exercise, nutrition, mindfulness (e.g., yoga), physical therapy and rehabilitation, acupuncture, biofeedback, massage, sleep position, sleep duration, and physical activities.

In various embodiments, the adjustments of the settings of the patient assistance device each as part of method 1300 (including methods 1530 and 1640) can be performed as closed-loop control of the delivery of the neurostimulation from the stimulation device. The loop can be closed, for example, by the patient using the patient assistance device and/or a patient programming device such as RC 632, by the patient assistance device communicating with the stimulation device directly, or by the patient assistance device communicating with the stimulation device through the by the patient assistance device communicating with the stimulation device directly. Such closed-loop control allows for optimization of the settings of the stimulation device periodically or as needed. For example, the patient assistance device can initiate an optimization process at a specified frequency (e.g., 1-3 days during which one or more non-invasive sensing devices are worn by the patient). The patient assistance device can also detect conditions for initiating the optimization process. For example, the patient assistance device can detect the patient's activity level or other indications of sleeping using the patient-specific monitoring information, and initiate the optimization process when the patient is sleeping or at rest.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for managing use of an implantable stimulation device using a network, the implantable stimulation device configured for delivering neurostimulation to a patient, the system comprising:
   one or more sensing devices configured to sense one or more signals from the patient, the one or more sensing devices including one or more non-invasive wearable sensing devices configured to be worn by the patient; and a patient assistance device configured to be communicatively coupled to the network and to assist the patient in use of the implantable stimulation device, the patient assistance device being a mobile device including:
- a communication circuit configured to receive the sensed one or more signals from the one or more sensing devices and to communicate with the implantable stimulation device;
- a user interface configured to allow for interactions between the patient assistance device and the patient; and
- a processing circuit configured to receive patient-specific information including the sensed one or more signals, to analyze the received patient-specific information with neurostimulation algorithm information representative of available therapeutic options including delivering spinal cord stimulation (SCS) using the implantable stimulation device, to produce one or more recommendations related to use of the implantable stimulation device for treating the patient based on one or more outcomes of the analysis, to transmit the produced one or more recommendations to a plurality of users through the network, to receive comments from the plurality of users through the network, and to present at least one recommendation of the produced one or more recommendations using the user interface, the at least one recommendation indicating, before the patient receives the SCS, whether implantation of the implantable stimulation device into the patient for delivering the SCS is recommended.

2. The system of claim 1, wherein the patient assistance device comprises a smartphone.

3. The system of claim 1, further comprising a remote control configured to be used by the patient to adjust the implantable stimulation device, wherein the communication circuit of the patient assistance device is configured to allow for one or more of direct communications between the patient assistance device and the remote control or direct communications between the patient assistance device and the implantable stimulation device.

4. The system of claim 3, wherein the one or more sensing devices further comprises one or more implantable sensing devices.

5. The system of claim 1, further comprising a plurality of databases and a telecommunication system configured to communicatively couple the patient assistance device to the plurality of databases, the plurality of databases including a patient database containing portions of the patient-specific information and a neurostimulation algorithm database containing portions of the neurostimulation algorithm information.

6. The system of claim 5, further comprising a plurality of web portals each configured to allow a type of users of a plurality of types of users to participate in the treatment of the patient using the implantable stimulation device.

7. The system of claim 6, wherein the processing circuit of the patient assistance device is further configured to produce at least one recommendation for initial settings of the implantable stimulation device including at least a type of the implantable stimulation device, a stimulation program, and parameters used by the stimulation program, to optimize the settings of the stimulation device for the patient after the neurostimulation is delivered to the patient, and to maintain optimization of the settings of the implantable stimulation device for the patient throughout the use of the implantable stimulation device for the patient.

8. The system of claim 6, wherein the processing circuit of the patient assistance device is further configured to detect a problem based on the patient-specific information received after the neurostimulation is delivered to the patient and to identify a user of the plurality of users who is suitable for addressing the detected problem based on a type of the detected problem, and to communicate to the identified user about the detected problem through the telecommunication system and a web portal of the plurality of web portals.

9. The system of claim 6, wherein the processing circuit of the patient assistance device is further configured to identify complementary activities and behaviors to be combined with the neurostimulation delivered from the implantable stimulation device to enhance outcome of the neurostimulation, and to recommend the identified activities and behaviors to the patient using the user interface of the patient assistance device.

10. A non-transitory machine readable medium including instructions, which when operated on by a mobile device, cause the mobile device to perform a method comprising:
- receiving one or more signals from one or more non-invasive sensing devices worn by a patient;
- receiving information through a network;
- analyzing patient-specific information with neurostimulation algorithm information, the patient-specific information including the one or more signals received from the one or more non-invasive sensing devices and the information received through the network, the neurostimulation algorithm information including available therapeutic options for delivering neurostimulation using an implantable stimulation device configured to be communicatively coupled to the mobile device and computational models configured for predicting outcome of the neurostimulation by simulations;
- producing one or more recommendations related to use of the implantable stimulation device for treating the patient based on one or more outcomes of the analysis;
- transmitting the produced one or more recommendations to a plurality of users through the network;
- receiving comments from the plurality of users through the network; and
- presenting at least one recommendation of the produced one or more recommendations to the patient, the at least one recommendation indicating, before the patient receives spinal cord stimulation (SCS), whether implantation of the implantable stimulation device into the patient for delivering SCS is recommended for treating the patient.

11. A method for managing use of an implantable stimulation device configured for delivering neurostimulation to a patient, comprising:
- sensing one or more signals from the patient using one or more non-invasive sensing devices worn by the patient;
- transmitting the sensed one or more signals to a patient assistance device provided to the patient, the patient assistance device configured to be communicatively coupled to the implantable stimulation device and to be communicatively coupled to a network;
- analyzing patient-specific information with neurostimulation algorithm information using the patient assistance device, the patient-specific information including the sensed one or more signals, the neurostimulation algorithm information representative of available therapeutic options using the implantable stimulation device;

producing one or more recommendations related to use of the implantable stimulation device for treating the patient based on one or more outcomes of the analysis;

transmitting the one or more recommendations to a plurality of users through the network;

receiving comments from the plurality of users through the network; and presenting at least one recommendation of the produced one or more recommendations to the patient, the at least one recommendation indicating, before the patient receives spinal cord stimulation (SCS), whether implantation of the implantable stimulation device into the patient for delivering SCS is recommended for treating the patient.

12. The method of claim 11, further comprising receiving the patient-specific information, including presenting one or more questions to the patient and receiving one or more answers from the patient using the patient assistance device.

13. The method of claim 12, wherein receiving the patient-specific information further comprises receiving information from a patient database accessible using the patient assistance device.

14. The method of claim 11, further comprising receiving the neurostimulation algorithm information from a neurostimulation algorithm database accessible using the patient assistance device.

15. The method of claim 11, wherein producing the one or more recommendations further comprises producing a recommendation for initial settings of the implantable stimulation device.

16. The method of claim 15, further comprising:
programming the implantable stimulation device based on the recommended initial settings; and
delivering neurostimulation from the programmed implantable stimulation device.

17. The method of claim 16, further comprising producing a recommendation for customizing the settings of the implantable stimulation device using the one or more signals sensed after a beginning of the delivery of the neurostimulation.

18. The method of claim 17, further comprising teaching the patient on how to adjust the settings of the implantable stimulation device using a touchscreen of the patient assistance device.

19. The method of claim 11, further comprising:
communicatively coupling the patient assistance device to a network including portals accessible by users each specialized in one or more fields related to the use of the implantable stimulation device;
identifying a problem associated with the use of the implantable stimulation device;
identifying a user from the users who is considered suitable for addressing the identified problem; and
notifying the identified user by one or more of communicating to the user through the network directly or presenting instructions on contacting the identified user using the patient assistance device.

20. The method of claim 11, further comprising implementing the patient assistance device as a mobile device.

* * * * *